(12) United States Patent
Talyansky et al.

(10) Patent No.: US 9,626,540 B1
(45) Date of Patent: Apr. 18, 2017

(54) SECURE WIRE MARKING FOR IDENTIFICATION AND AUTHENTICATION

(71) Applicants: Vitaly Talyansky, Portland, OR (US); Edward Talyansky, Battle Ground, WA (US); Jose Gasque, Vancouver, WA (US)

(72) Inventors: Vitaly Talyansky, Portland, OR (US); Edward Talyansky, Battle Ground, WA (US); Jose Gasque, Vancouver, WA (US)

( * ) Notice: Subject to any disclaimer, the term of this patent is extended or adjusted under 35 U.S.C. 154(b) by 0 days.

(21) Appl. No.: 15/093,649

(22) Filed: Apr. 7, 2016

(51) Int. Cl.
*G01N 21/64* (2006.01)
*G06K 7/10* (2006.01)
*G06K 7/14* (2006.01)
*G06K 19/06* (2006.01)

(52) U.S. Cl.
CPC ......... *G06K 7/10732* (2013.01); *G01N 21/64* (2013.01); *G06K 7/1417* (2013.01); *G06K 19/06037* (2013.01)

(58) Field of Classification Search
CPC ........ G01V 15/00; B82Y 15/00; G06K 19/00; G06K 17/077; G06K 19/14
See application file for complete search history.

(56) References Cited

U.S. PATENT DOCUMENTS

| | | | |
|---|---|---|---|
| 8,009,893 B2 * | 8/2011 | Rhoads ................. | G06T 1/0064 283/85 |
| 9,360,589 B1 * | 6/2016 | Meinhold ............ | G01N 21/643 |
| 2007/0065609 A1 * | 3/2007 | Korson ................ | B65D 55/026 428/34.1 |
| 2010/0209632 A1 * | 8/2010 | Weisman ............... | B82Y 25/00 428/29 |

\* cited by examiner

*Primary Examiner* — Kiho Kim (57) ABSTRACT

Secure wire marking for identification and authentication is disclosed herein. An example apparatus includes a first strand that is electrically conductive, the first strand being embedded with a first set of particles, wherein the first set of particles have a first optical response when they are illuminated by light having a first wavelength.

13 Claims, 10 Drawing Sheets

SECURE WIRE MARKING FOR IDENTIFICATION AND AUTHENTICATION

FIELD OF THE DISCLOSURE

The present disclosure relates generally to product authentication and protection, and more particularly, to secure wire marking for identification and authentication.

BACKGROUND

Conductive wires are a valuable commodity. As such, wires are often stolen or counterfeited.

DETAILED DESCRIPTION

Counterfeit products can cause significant economic and other damage to both the purveyor of authentic non-counterfeit products and consumers of the counterfeit products. One product that is often counterfeited is electrically conductive wires. Such wires are used in cables for consumer electronic, in commercial or industrial devices, to wire homes for electricity and for many other purposes. These wires can be counterfeited and sold by unscrupulous manufacturers. In addition to potential economic damage, this can be dangerous if an improper wire is used in certain situations.

In addition to counterfeiting, wires can be stolen from places like construction sites or warehouses. Since wires are often made of copper, aluminum or other metals, stolen wire can have economic value that may encourage theft. Stolen wire can be resold at scrap yards or other locations.

One method to combat both theft and counterfeiting of wires is to include identifying information on the wires that can be checked to authenticate a wire. Counterfeit wires would not have this identifying information and therefore authentic wires could be identified and verified as authentic and not counterfeit. In addition, a scrapyard or other entity that is concerned about purchasing stolen wire can check the wire for the identifying information to identify stolen wire.

Furthermore, identifying information can be used to distinguish different types of wire by placing different identifiers on the various types of wire. The identifying information can later be checked by a user of the wire to ensure that they are using the proper type of wire. This would avoid potential problems with mislabeled wire or wire with missing or incomplete labels.

Visual indicators on wires could be used for the above purposes. However, visual indicators can be easily viewed and reproduced by counterfeiters or removed from stolen wire by thieves in order to defeat the security. Alternatively, invisible indicators would not be visible to counterfeiters and thieves and would be more difficult for them to reproduce or remove. These invisible indicators could be detected by a specialized device to authenticate and/or identify the wire.

One type of invisible indicator or marker that can be used on a wire is an inorganic ceramic material known as a luminophor or phosphor. Luminophors have the optical property of luminescence. Luminescence is a physical property of certain materials that manifests in such a way that when a luminophor is illuminated with light of a particular wavelength (the luminophor's excitation wavelength), it emits light at a different wavelength (the luminophor's emission wavelength). By coating a wire with a luminophor or embedding a luminophor into a wire, the luminophor can be detected in the wire by illuminating the wire with light at the appropriate excitation wavelength and detecting emitted light at the corresponding emission wavelength. Furthermore, luminophors are microscopic in size and invisible to the naked eye.

Additionally, different luminophors with different excitation and emission wavelengths can be used to identify different types of wires. Alternatively, luminophors can be printed on a wire in different patterns to effectively create an invisible identifier or barcode that can be viewed by illuminating the wire with light at the excitation wavelength of the luminophor used to coat the wire and detecting the luminescent response at the luminophor's emission wavelength. Additionally, absorbers can be used rather than luminophors to mark an authentic wire. Absorbers absorb light at a particular wavelength and can be detected by illuminating a wire with light at this absorption wavelength and detecting the reflection. A wire that contains absorbers will not reflect this light.

Example methods, apparatus, and/or articles of manufacture disclosed herein provide secure wire marking for identification and authentication. In examples disclosed herein, luminophors with luminescent properties are embedded in an electrically conductive wire. In examples disclosed herein, these luminophors have a known excitation wavelength and a known emission wavelength such that the luminophors emit light at the emission wavelength when they are illuminated by light at the excitation wavelength. In examples disclosed herein, a wire is authenticated by illuminating it with light at the appropriate wavelength and detecting a luminescent response. In examples disclosed herein, luminophors may be embedded or printed onto a wire in a particular pattern that can be discerned only by detecting the luminescent emission of the phosphors. In some examples disclosed herein, the exact position of the phosphors on a wire is used to specifically identify the wire. In some examples, a wire is embedded with two or more luminophors with different excitation and emission wavelengths to increase the level of security in marking the wire. In these examples, both luminophors would be detected in order to authenticate the wire. In some examples herein, absorbers are used to mark a wire as authentic. In these examples, a wire is illuminated with light at the absorption wavelength of the absorbers and the reflection detected from the wire is measured to determine whether absorbers are present.

Figure 1:
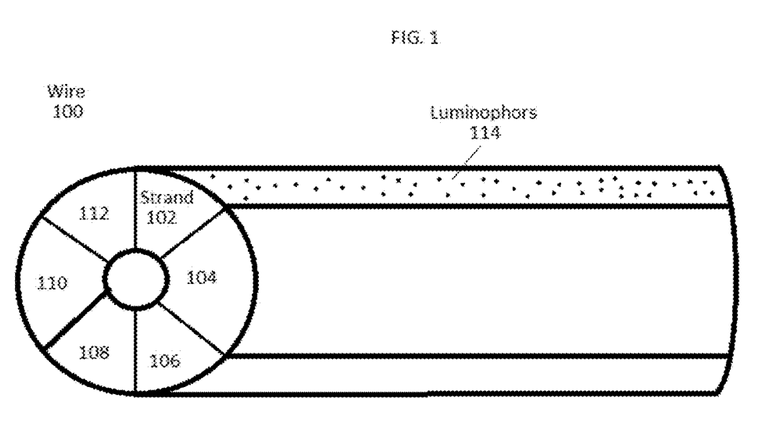
FIG. 1 is a block diagram of a wire marked for identification and authentication in accordance with the teachings of this disclosure.

FIG. 1 is a block diagram of a wire 100 marked for identification and authentication in accordance with the teachings of this disclosure. The example wire 100 is an electrically conductive wire. In other examples, the wire 100 may be any type of extruding material including a plastic, metal or any other type of material or object. In the illustrated example, the wire 100 consists of multiple strands 102, 104, 106, 108, 110 and 112. In some examples, the wire 100 consists of a single strand. In the illustrated example, strand 102 contains embedded luminophors 114. In some examples, multiple strands contain embedded luminophors. In the illustrated example, the luminophors 114 are embedded throughout strand 102.

In the illustrated example, the luminophors 114 have luminescent properties such that when they are illuminated by light at a certain excitation wavelength, they emit light at a particular emission wavelength. The example luminophors 114 are less than one micron in diameter and are invisible to the naked eye. In some examples, different wires are marked with luminophors that have different excitation and emission wavelengths such that each marked wire can be specifically identified by detecting the luminescent response to various excitation wavelengths.

In the illustrated example, the luminophors 114 are produced as a powder and mixed with a lubricating oil that is used to coat the strand 102 of the wire 100. In this way, the example luminophors 114 become embedded in the example strand 102 of the example wire 100 when the lubricating oil is applied to the wire 100 as part of the manufacturing process of the wire 100. In some examples, the luminophors 114 are mixed with other fluids used in processing the wire 100. In other examples, the luminophors 114 are mixed with ink that is used in a continuous inkjet printer or other type of printer. In these examples, this ink is printed onto the example strand 102 of the example wire 100 embedding the example luminophors 114 therein. In other examples, other methods of embedding the example luminophors 114 into the example strand 102 of the example wire 100 may be used. In the illustrated example, the luminophors 114 are embedded equally across the length of the strand 102 of the wire 100. In some examples, the luminophors 114 are embedded into only a portion of the strand 102 of the wire 100. In some examples, the luminophors 114 are embedded into multiple strands of the wire 100.

Figure 2:
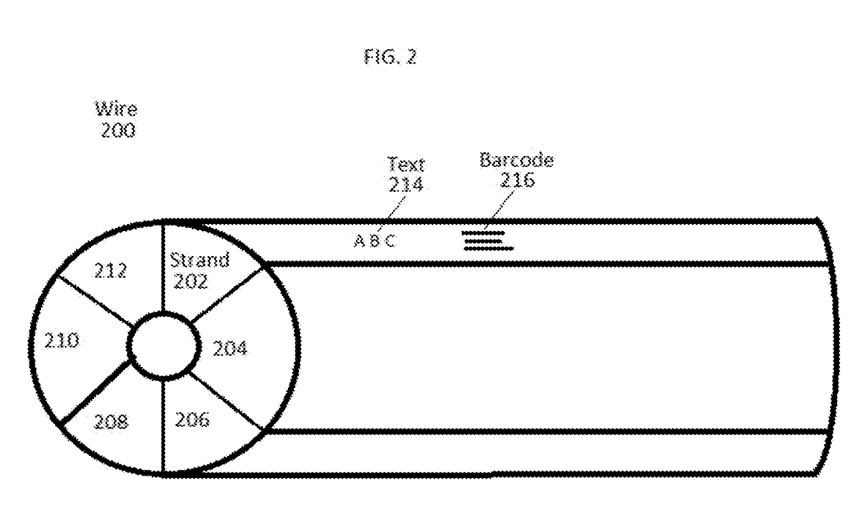
FIG. 2 is a block diagram of a wire marked for identification and authentication in accordance with the teachings of this disclosure.

FIG. 2 is a block diagram of a wire 200 marked for identification and authentication in accordance with the teachings of this disclosure. In the illustrated example, the wire 200 is an electrically conductive wire containing strands 202, 204, 206, 208, 210 and 212. In the illustrated example, strand 202 is marked with luminophors in particular patterns. In the illustrated example, strand 202 of the wire 200 is embedded with luminophors in the pattern of text 214 and barcode 216. In other examples, luminophors can be embedded into strand 202 or other strands of wire 200 in any desired pattern. Using luminophors to mark the wire 200 allows identifying or other information to be placed on the wire 200 without making those markings viewable to unauthorized users.

In the illustrated example, text 214 and barcode 216 are printed onto strand 202 of wire 200 with a continuous inkjet printer using ink mixed with luminophors. In other examples, different methods of embedding luminophors into strand 202 of wire 200 in patterns may be used. In the illustrated example, the luminophors used for patterns 214 and 216 are less than one micron in diameter and are invisible to the naked eye. Therefore, the patterns 214 and 216 on strand 202 of wire 200 are invisible to the naked eye. In the illustrated example, the luminophors used for markings 214 and 216 have a luminescent response such that they emit light at a specific emission wavelength when illuminated by light at a particular excitation wavelength. This allows the example patterns 214 and 216 to be viewed only when illuminated with light at the correct wavelength.

In the illustrated example, the markings 214 and 216 are each printed once on strand 202 of wire 200. In some examples, markings are printed at multiple locations on strand 202. In some examples, a marking is repeated many times over the length of strand 202. In some examples, different markings are printed at different locations on strand 202. In some examples, markings are printed on multiple strands of wire 200.

Figure 3:
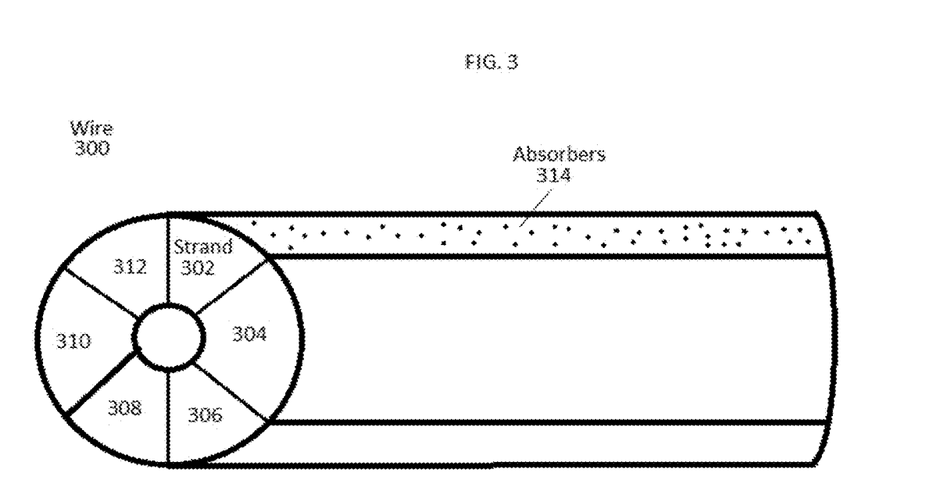
FIG. 3 is a block diagram of a wire marked for identification and authentication in accordance with the teachings of this disclosure.

FIG. 3 is a block diagram of a wire 300 marked for identification and authentication in accordance with the teachings of this disclosure. The example wire 300 is an electrically conductive wire containing strands 302, 304, 306, 308, 310 and 312. In some examples, the wire 300 consists of a single strand. In the illustrated example, strand 302 contains embedded absorbers 314. These example absorbers 314 are particles that absorb light at a particular wavelength. In some examples, multiple strands contain embedded absorbers. In the illustrated example, the absorbers 314 are embedded throughout strand 302.

Figure 4:
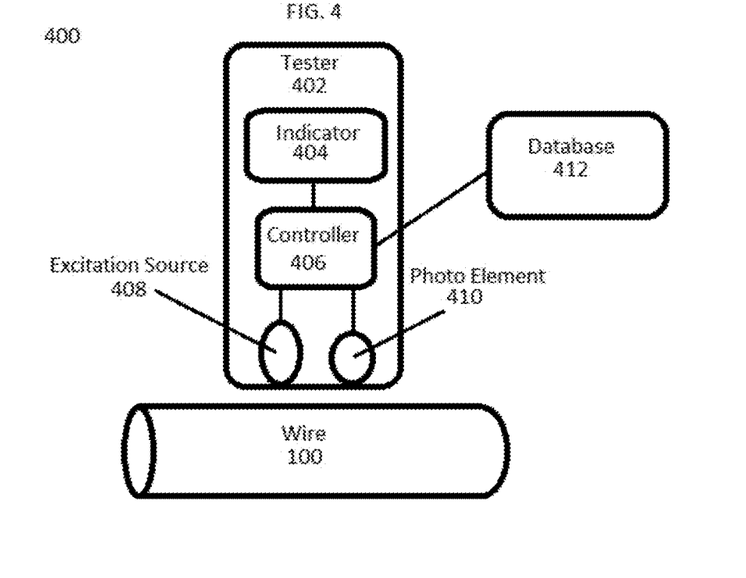
FIG. 4 is a block diagram of a system utilizing secure wire marking for identification and authentication in accordance with the teachings of this disclosure.

FIG. 4 is a block diagram of a system 400 utilizing secure wire marking for identification and authentication in accordance with the teachings of this disclosure. The example system 400 includes the wire 100 of FIG. 1, which has a strand 102 embedded with luminophors 114 and a tester 402. The example tester 402 includes an indicator 404, a controller 406, an excitation source 408, a photo element 410 and a database 412. In some examples, the system 400 is used with the wire 200 from FIG. 2 or the wire 300 from FIG. 3 rather than the wire 100 from FIG. 1.

In the illustrated example of FIG. 4, the excitation source 408 illuminates the wire 100 with light at the excitation wavelength of the luminophors 114. In the illustrated example, the excitation source 408 is a light emitting diode. In other examples, the excitation source 408 can be a laser or any other source capable of emitting light at the appropriate wavelength.

The example photo element 410 detects light at the emission wavelength of the example luminophors 114. In the illustrated example, the photo element 410 is a photodiode. In other examples, any type of photo element 410 can be used that is capable of detecting light at the appropriate wavelengths.

The example indicator 404 indicates to a user the results of an authentication of the wire 100. In the illustrated example, the indicator 404 indicates a positive response if the photo element 410 detects a luminescent response from the wire 100 after the excitation source 408 illuminates the wire 100. The example indicator 404 may provide an audio indication, a visual indication or any other type of indication to a user of the example tester 402. In some examples, the indicator 404 displays an image of the luminophor pattern captured by the example photo element 410. This is useful for wires such as the example wire 200 of FIG. 2 that contain luminophors printed in or more patterns on the wire.

The example controller 406 communicates with and controls the example indicator 404, the example excitation source 408, the example photo element 410 and the example database 412. The example controller 406 controls the timing of the operation of the various components in order to properly authenticate the wire 100 and determine whether any luminophors 114 are present in the wire 100.

In the illustrated example, the database 412 stores data sent by the controller 406 such as the position of luminophors on a wire. The example database 412 also sends data to the example controller 406 to compare data detected by the tester 402 against previously stored data. This allows a tester to determine if the example wire 100 matches a specific wire or type of wire that was previously scanned and had certain data from it stored in the example database 412.

While an example manner of implementing the secure wire marking for identification and authentication has been illustrated in FIGS. 1-4, one or more of the elements, processes and/or devices illustrated in FIGS. 1-4 may be combined, divided, re-arranged, omitted, eliminated and/or implemented in any other way. Further, the example indicator 404, the example controller 406, the example excitation source 408, the example photo element 410, the example database 412 and/or, more generally, the example tester 402 of FIG. 4 may be implemented by hardware, software, firmware and/or any combination of hardware, software and/or firmware. Thus, for example, any of the example indicator 404, the example controller 406, the example excitation source 408, the example photo element 410, the example database 412 and/or, more generally, the example tester 402 of FIG. 4 could be implemented by one or more circuit(s), programmable processor(s), application specific integrated circuit(s) (ASIC(s)), programmable logic device(s) (PLD(s)), microprocessor(s), hardware processor(s), and/or field programmable logic device(s) (FPLD(s)), etc. When any of the system or apparatus claims of this patent are read to cover a purely software and/or firmware implementation, at least one of the example indicator 404, the example controller 406, the example excitation source 408, the example photo element 410, the example database 412 and/or, more generally, the example tester 402 of FIG. 4 is hereby expressly defined to include a tangible computer readable storage medium such as a memory, DVD, CD, Blu-ray, etc. storing the software and/or firmware. Further still, the example indicator 404, the example controller 406, the example excitation source 408, the example photo element 410, the example database 412 and/or, more generally, the example tester 402 of FIG. 4 may include more than one of any or all of the illustrated elements, processes and devices.

Figure 5:
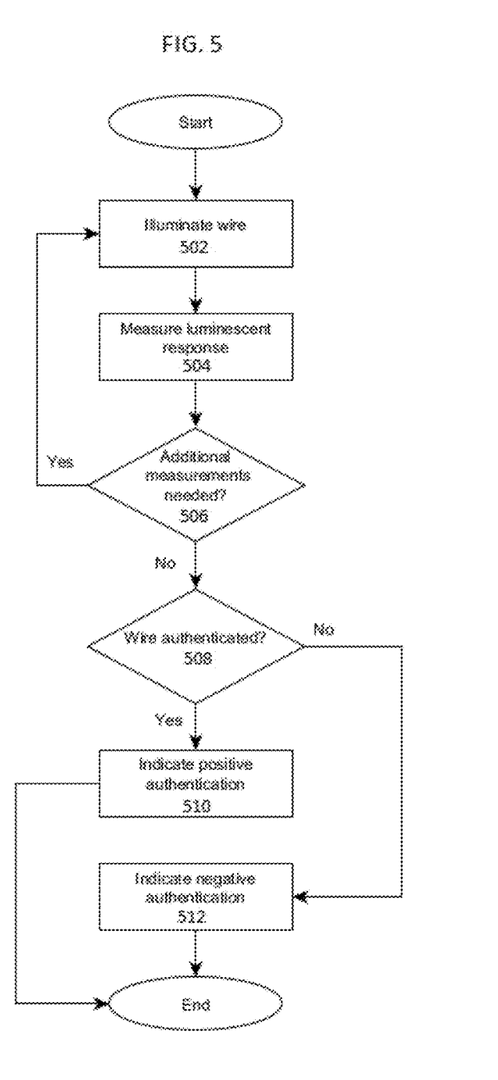
FIG. 5 is a flowchart representative of example machine readable instructions that may be executed to implement the example system of FIG. 4.
Figure 6:
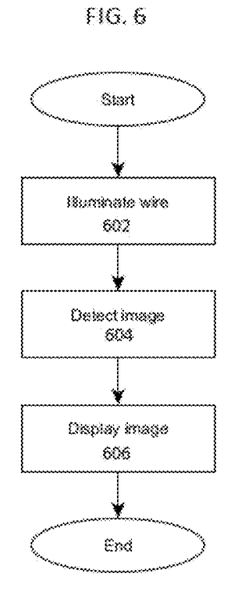
FIG. 6 is a flowchart representative of example machine readable instructions that may be executed to implement the example system of FIG. 4.
Figure 7:
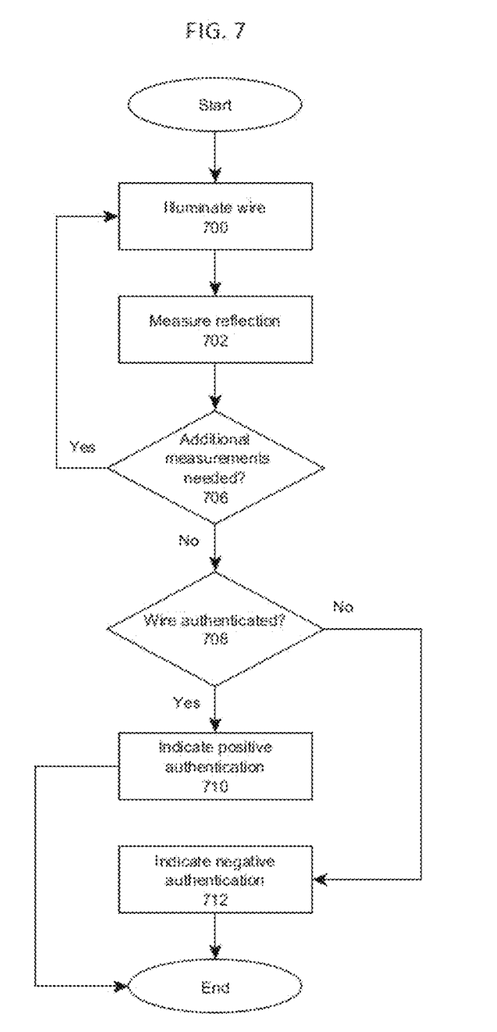
FIG. 7 is a flowchart representative of example machine readable instructions that may be executed to implement the example system of FIG. 4.
Figure 8:
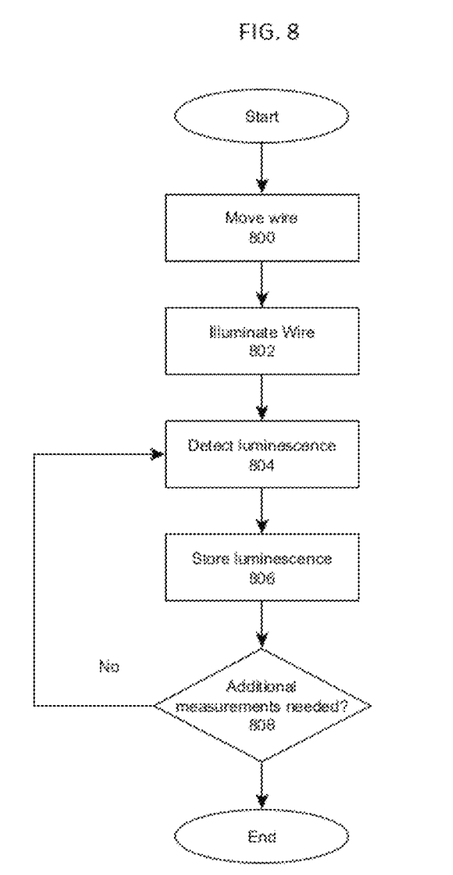
FIG. 8 is a flowchart representative of example machine readable instructions that may be executed to implement the example system of FIG. 4.
Figure 9:
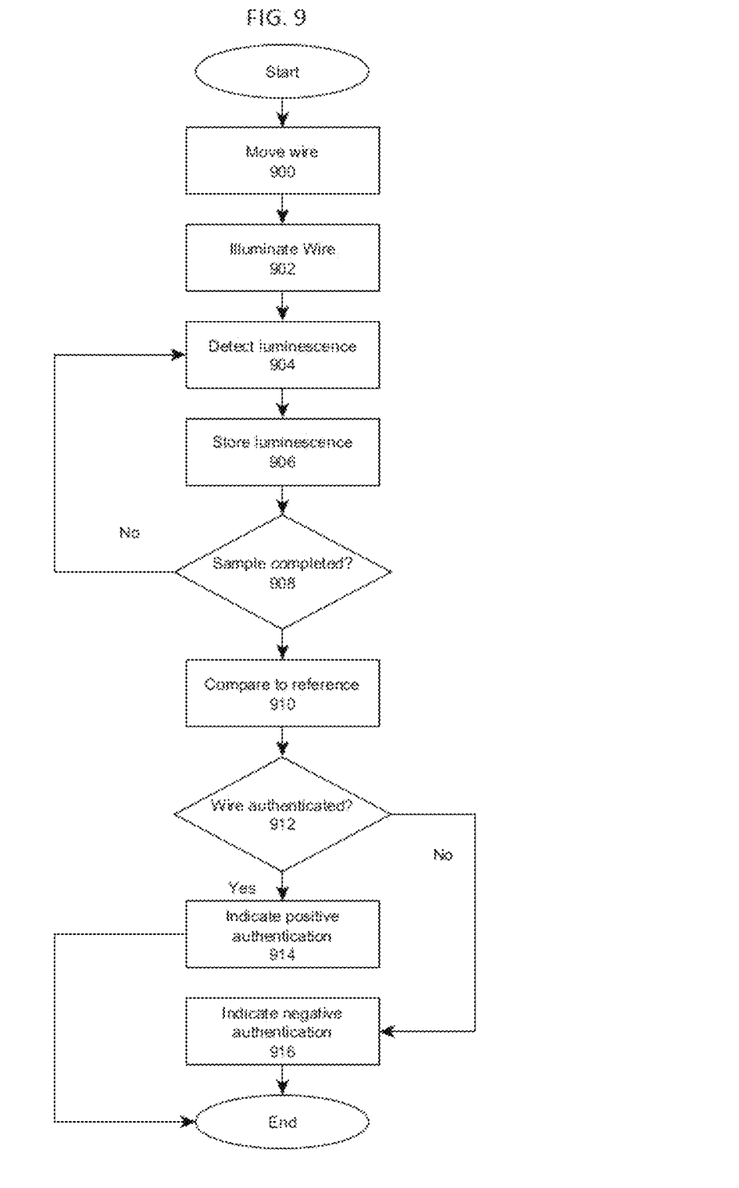
FIG. 9 is a flowchart representative of example machine readable instructions that may be executed to implement the example system of FIG. 5.

FIGS. 5-9 are flowcharts representative of example machine readable instructions for implementing the example system 400 of FIG. 4. Specifically, the example of FIG. 5 is a flowchart of instruction to determine whether a wire contains luminophors and is therefore authentic. The example of FIG. 6 is a flowchart of instructions to view a pattern of luminophors embedded on a wire. The example of FIG. 7 is a flowchart of instructions to determine whether a wire contains absorbers. The example of FIG. 8 is a flowchart of instructions to detect an arrangement of luminophors on a wire and store that information. The example of FIG. 9 is a flowchart of instructions to detect an arrangement of luminophors on a wire and compare it to a stored arrangement. In the example flowcharts of FIGS. 5-9, the machine readable instructions comprise program(s) for execution by a processor such as the processor 1012 shown in the example computer 1000 discussed below in connection with FIG. 10. The program(s) may be embodied in software stored on a tangible computer readable storage medium such as a CD-ROM, a floppy disk, a flash drive, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program(s) is described with reference to the flowcharts illustrated in FIGS. 5-9, many other methods of implementing the example system 400 of FIG. 4 may alternatively be used. For example, the order of execution of the blocks may be changed, and/or some of the blocks described may be changed, eliminated, or combined.

As mentioned above, the example processes of FIGS. 5-9 may be implemented using coded instructions (e.g., computer readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable storage medium is expressly defined to include any type of computer readable storage device and/or disk and to exclude propagating signals. Additionally or alternatively, the example processes of FIGS. 5-9 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable storage medium is expressly defined to include any type of computer readable storage device and/or disk and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 5 begins when the example excitation source 408 illuminates the example wire 100 with light at the excitation wavelength of the luminophors 114 embedded in the wire 100 (block 502). In the illustrated example, the excitation source 408 illuminates the wire 100 for a specific short duration of time. If the wire 100 is authentic and the example luminophors 114 are embedded in the wire 100, this illumination causes a luminescent response and the luminophors 114 will emit light at their excitation wavelength. The example photo element 410 then measures this luminescent response (block 504).

After the example photo element 410 measures the luminescent response emitted by the example wire 100, the example controller 406 determines whether additional measurements are needed (block 506). In the illustrated example, the excitation source 408 emits a series of pulses of light to repeatedly illuminate the wire 100 and the luminescent response of the wire 100 is measured after each pulse. In some examples, the excitation source 408 only illuminates the wire 100 once. In some examples, the controller 406 decides whether to illuminate the wire 100 additional times based on the luminescent response detected by the photo element 410. If the example controller 406 determines that additional measurements are needed (block 506), control returns to block 502 and the excitation source 408 illuminates the wire 100 again. If the example controller 406 determines that no additional measurements are needed (block 506), control passes to block 508.

After the example controller 406 determines that additional measurements are not needed (block 506), the controller 406 determines whether the wire 100 is authentic (block 508). In the illustrated example, the controller 406 determines that the wire 100 is authentic if the luminescent response measured by the photo element 410 is above a certain threshold. In other examples, other methods of determining whether the wire 100 is authentic based on the luminescent response measured by the photo element 410 may be used. If the example controller 406 determines that the example wire 100 is authentic (block 508), control passes to block 510 and the example indicator 404 gives an indication that the wire is authentic. If the example controller 406 determines that the example wire 100 is not authentic (block 508), control passes to block 512 and the example indicator 404 gives an indication that the wire is not authentic. After the example indicator indicates either a positive or a negative authentication, the example of FIG. 5 ends.

FIG. 6 is a flowchart representative of another set of example machine readable instructions for implementing the example system 400 of FIG. 4. Specifically, the example of FIG. 6 is used to view luminophors embedded on a wire 200 in a particular pattern as in the example of FIG. 2.

FIG. 6 begins when the example excitation source 408 illuminates the example wire 200 with light at the excitation source of the luminophors 214 or 216 embedded in the wire 200 (block 602). The example photo element 410 then detects a spatial two-dimensional image of the pattern of the example luminophors 214 or 216 embedded in the example wire 200 (block 604). The example indicator 404 then displays a visual image of the pattern of example luminophors 214 or 216 detected by the example photo element 410 (block 606). The example of FIG. 6 then ends.

FIG. 7 is a flowchart representative of another set of example machine readable instructions for implementing the example system 400 of FIG. 4. Specifically, the example of FIG. 7 is used to determine whether absorbers 314 are present in an example wire 300.

FIG. 7 begins when the example excitation source 408 illuminates the example wire 300 with light at the absorption wavelength of the example absorbers 314 embedded in the wire 300 (block 700). In the illustrated example, the excitation source 408 illuminates the wire 300 for a specific short duration of time. If the wire 300 is authentic and the example absorbers 314 are embedded in the wire 300, this illuminating light will be absorbed by the absorbers 314. If the wire 300 is not authentic and there are no absorbers present, the illuminating light will be reflected back off of the wire 300. The example photo element 410 then measures this reflectance (block 702).

After the example photo element 410 measures the reflectance off of the example wire 300, the example controller 406 determines whether additional measurements are needed (block 706). In the illustrated example, the excitation source 408 emits a series of pulses of light to repeatedly illuminate the wire 300 and the reflectance off of the wire 300 is measured after each pulse. In some examples, the excitation source 408 only illuminates the wire 300 once. In some examples, the controller 406 decides whether to illuminate the wire 300 additional times based on the reflectance detected by the photo element 410. If the example controller 406 determines that additional measurements are needed (block 706), control returns to block 700 and the excitation source 408 illuminates the wire 300 again. If the example controller 406 determines that additional measurements are not needed (block 706), control passes to block 708.

After the example controller 406 determines that additional measurements are not needed (block 706), the controller 406 determines whether the wire 300 is authentic (block 708). In the illustrated example, the controller 406 determines that the wire 300 is authentic if the reflectance measured by the photo element 410 is above a certain threshold. In other examples, other methods of determining whether the wire 300 is authentic based on the reflectance measured by the photo element 410 may be used. If the example controller 406 determines that the example wire 300 is authentic (block 708), control passes to block 710 and the example indicator 404 gives an indication that the wire 300 is authentic. If the example controller 406 determines that the example wire 300 is not authentic (block 708), control passes to block 712 and the example indicator 404 gives an indication that the wire is not authentic. After the example indicator indicates either a positive or a negative authentication, the example of FIG. 7 ends.

FIG. 8 is a flowchart representative of another set of example machine readable instructions for implementing the example system 400 of FIG. 4. Specifically, the example of FIG. 8 is used to store the precise locations of the example luminophors 114 on the example wire 100 in FIG. 1. Because the luminophors have a particle size of less than one micron and are embedded in the example wire 100 by first mixing them in ink or lubricating oil, they will be randomly distributed across the wire 100 after they are applied. Therefore, each wire in which luminophors are embedded will have slightly different arrangement of those luminophors on the wire. Capturing and storing the particular arrangement of luminophors on a wire will allow that specific wire to be later identified by comparing its arrangement of luminophors to the arrangement previously stored.

FIG. 8 begins when the example wire 100 is moved along a path under the example tester 402 (block 800). In the illustrated example, the wire 100 is moved by a machine at a constant rate of speed under the tester 402. In some examples, the wire 100 is moved through or under a tester with multiple excitation sources and photo elements in order to detect luminophors on the wire from multiple angles. After the example wire 100 begins to move along the path under the example tester 402, the example excitation source 408 emits light at the excitation wavelength of the example luminophors 114 (block 802). The example photo element 410 then detects the luminescent emission from the example wire 100 (block 804). Because the example wire 100 is moving during this procedure, the photo element 410 will illuminate a specific position on the wire 100 and the photo element 410 will detect the luminescent emission for that particular position on the wire 100. The strength of the luminescent emission at that position on the example wire 100 is then stored in the example database 412 (block 806).

After the luminescent emission for a particular position on the example wire 100 is stored in the example database 412

(block 806), the example controller 406 determines if additional measurements are needed (block 808). The example controller 406 determines that no additional measurements are needed when the example wire 100 has completed its movement path under the example tester 402 and the entire wire 100 has been imaged by this procedure. If the example controller 406 determines that additional positions on the example wire 100 need to be imaged (block 808), then control returns to block 804 and the example excitation source 408 illuminates the wire 100 at the next position that the wire has moved to. Eventually, the luminescence will be detected and stored for multiple positions on the example wire 100 and the example database 412 will contain a profile of the distribution of the example luminophors 114 along the wire 100. If the example controller 406 determines that no additional measurements are needed (block 808), the example of FIG. 8 ends.

FIG. 9 is a flowchart representative of another set of example machine readable instructions for implementing the example system 400 of FIG. 4. Specifically, the example of FIG. 9 is used to compare the positions of luminophors on a sample wire to the positions of luminophors stored in a database that were previously measured for a control wire. This allows for a determination of whether the sample wire being imaged is actually the control wire that was previously imaged. as stored in the database. This procedure can be used to not only tell whether a wire is authentic and not counterfeit but also to specifically identify a wire for forensic analysis or other purposes.

FIG. 9 begins when the example sample wire 100 is moved along a path under the example tester 402 (block 900). In the illustrated example, the wire 100 is moved by a machine at a constant rate of speed under the tester 402. In some examples, the wire 100 is moved through or under a tester with multiple excitation sources and photo elements in order to detect luminophors on the wire from multiple angles. After the example wire 100 begins to move along the path under the example tester 402, the example excitation source 408 emits light at the excitation wavelength of the example luminophors 114 (block 902). The example photo element 410 then detects the luminescent emission from the example wire 100 (block 904). Because the example wire 100 is moving during this procedure, the photo element 410 will illuminate a specific position on the wire 100 and the photo element 410 will detect the luminescent emission for that particular position on the wire 100. The strength of the luminescent emission at that position on the example wire 100 is then stored by the example controller 406 (block 906).

The example controller 406 then determines if the measurement sample for the sample wire is complete or if additional measurements are needed. In some examples, the entire sample wire is imaged and compared against the previously stored data for the control wire. In some examples, only a portion of the sample wire is imaged and compared against a subset of the stored data for the control wire. The example controller 406 determines that the sample is completed after the desired portion of the sample wire is imaged. If the example controller 406 determines that the sample is not completed (block 908), control returns to block 904 and additional measurements are taken for additional positions on the sample wire. If the example controller 406 determines that the sample is complete and no additional measurements are needed (block 908), control passes to block 910.

After the example controller 406 determines that all desired measurements have been taken for the desired sample (block 908), the measured luminophor positions stored by the controller 406 for the sample wire are compared against the luminophor positions stored by the example database 412 for the control wire (block 910). In some examples, measurements stored by the controller 406 are compared against the data for the entire control wire stored by the database 412. In other examples, the measurements stored by the controller 406 are compared against a subset of the data stored by the database 412 for the control wire. The example controller 406 then determines whether the sample wire is the authentic control wire by determining whether the measurements stored by the controller 406 for the sample wire match the measurements stored in the database 412 for the control wire (block 912). If the example controller 406 determines that the wire matches the control wire and is authentic (block 912), the example indicator 404 gives a positive indication (block 914). If the example controller 406 determines that the sample wire does not match the control wire and is not authentic (block 912), the example indicator 404 gives a negative indication (block 916). The example of FIG. 9 then ends.

Figure 10:
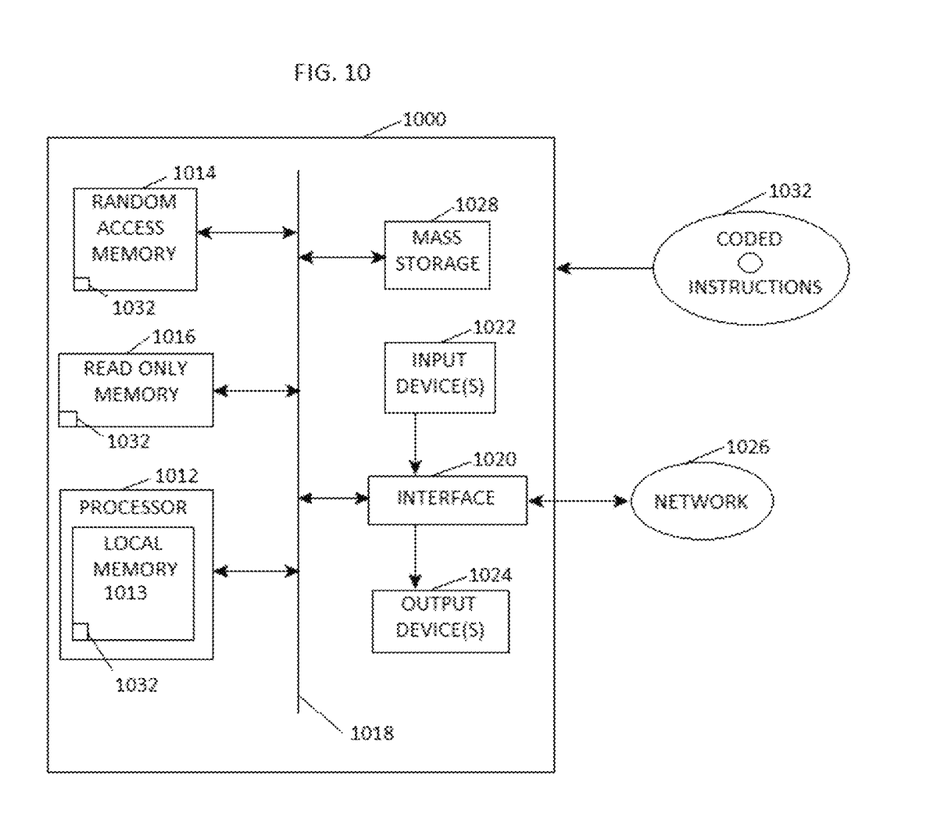
FIG. 10 is a block diagram of an example processing system capable of executing the example machine readable instructions of FIG. 5-9 to implement the example system of FIG. 4.

FIG. 10 is a block diagram of a processor platform 1000 capable of executing the instructions of FIGS. 5-9 to implement the example system of FIG. 4. The processor platform 1000 can be, for example, a server, a personal computer, an Internet appliance, a DVD player, a CD player, a Blu-ray player, a gaming console, a personal video recorder, a smart phone, a tablet, a printer, or any other type of computing device.

The processor platform 1000 of the instant example includes a processor 1012. As used herein, the term "processor" refers to a logic circuit capable of executing machine readable instructions. For example, the processor 1012 can be implemented by one or more microprocessors or controllers from any desired family or manufacturer.

The processor 1012 includes a local memory 1013 (e.g., a cache) and is in communication with a main memory including a volatile memory 1014 and a non-volatile memory 1016 via a bus 18. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a memory controller.

The processor platform 1000 also includes an interface circuit 1020. The interface circuit 1020 may be implemented by any type of interface standard, such as an Ethernet interface, a universal serial bus (USB), and/or a PCI express interface.

One or more input devices 1022 are connected to the interface circuit 1020. The input device(s) 1022 permit a user to enter data and commands into the processor 1012. The input device(s) can be implemented by, for example, a keyboard, a mouse, a touchscreen, a track-pad, a trackball, isopoint and/or a voice recognition system.

One or more output devices 1024 are also connected to the interface circuit 1020. The output devices 1024 can be implemented, for example, by display devices (e.g., a liquid crystal display, a cathode ray tube display (CRT), a printer and/or speakers). The interface circuit 1020, thus, typically includes a graphics driver card.

The interface circuit 1020 also includes a communication device such as a modem or network interface card to facilitate exchange of data with external computers via a network 1026 (e.g., an Ethernet connection, a digital subscriber line (DSL), a telephone line, coaxial cable, a cellular telephone system, etc.).

The processor platform 1000 also includes one or more mass storage devices 1028 for storing software and data. Examples of such mass storage devices 1028 include floppy disk drives, hard drive disks, compact disk drives and digital versatile disk (DVD) drives.

The coded instructions 1032 of FIG. 10 may be stored in the mass storage device 1028, in the volatile memory 1014, in the non-volatile memory 1016, and/or on a removable storage medium such as a CD or DVD.

Although certain example apparatus, methods, and articles of manufacture have been disclosed herein, the scope of coverage of this patent is not limited thereto. On the contrary, this patent covers all apparatus, methods, and articles of manufacture fairly falling within the scope of the claims of this patent.

What is claimed is:

1. A wire comprising:
a first strand that is electrically conductive, and a first set of inorganic ceramic particles embedded in the first strand having luminescent properties such that they emit light having a first wavelength when they are illuminated by light having a second wavelength.

2. The wire of claim 1, further comprising a second strand that is not embedded with the first set of particles.

3. The wire of claim 1, wherein the first strand is embedded with a second set of particles, the second set of particles having luminescent properties such that they emit light having a third wavelength when they are illuminated by light having a fourth wavelength.

4. The wire of claim 1, wherein the first set of particles are arranged on the first strand in a first pattern.

5. The wire of claim 1, wherein the first set of particles are embedded in the first strand via a first fluid applied to the first strand.

6. The wire of claim 5, wherein the first fluid is a lubricating oil.

7. A method comprising:
illuminating a first position on a first strand of a first electrically conductive wire with a first light having a first wavelength, the first strand containing embedded inorganic ceramic particles having a luminescent response such that they emit light having a second wavelength when they are illuminated by light having a first wavelength;
detecting a first strength of the luminescent response after the first position on the first strand is illuminated with light at the first wavelength;
illuminating a second position on the first strand with light having the first wavelength;
detecting a second strength of the luminescent response after the second position on the first strand is illuminated with light at the first wavelength;
performing a first comparison between the first and second strengths and a first set of values in a database; and
determining a property of the first wire based on the first comparison.

8. The method of claim 7, wherein the first set of values in a database correspond to strengths of luminescent responses measured after illuminating a strand of an electrically conductive wire with the first light at two positions on the wire.

9. The method of claim 7, further comprising determining whether the first wire is authentic based on the first comparison.

10. The method of claim 7, further comprising:
illuminating an additional set of positions on the first strand with the first light;
detecting a first set of strengths corresponding to the strength of the luminescent response after each of the additional set of positions on the first strand is illuminated with the first light;
performing a second comparison between the first set of strengths and a second set of values in database; and
determining a property of the first electrically conductive wire based on the second comparison.

11. The method of claim 10, wherein the first set of values corresponds to a set of luminescent strengths measured after illuminating multiple positions on a wire with light at the first wavelength.

12. The method of claim 7, wherein the first wavelength is in the electromagnetic portion of the electromagnetic spectrum.

13. The method of claim 7, wherein the second wavelength is in the infrared portion of the electromagnetic spectrum.

* * * * *